United States Patent
Ralfs et al.

(10) Patent No.: US 9,981,095 B2
(45) Date of Patent: May 29, 2018

(54) PROCESS FOR OPERATING A RESPIRATOR OR ANESTHESIA DEVICE IN THE APRV MODE TAKING INTO THE IMPEDANCE AND/OR THE IMPEDANCE CHANGE

(75) Inventors: Frank Ralfs, Lübeck (DE); Eckhard Teschner, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 3092 days.

(21) Appl. No.: 12/199,204

(22) Filed: Aug. 27, 2008

(65) Prior Publication Data

US 2009/0114222 A1 May 7, 2009

(30) Foreign Application Priority Data

Nov. 2, 2007 (DE) .................. 10 2007 052 472

(51) Int. Cl.
*A61M 16/00* (2006.01)
*A61B 5/053* (2006.01)

(52) U.S. Cl.
CPC ....... *A61M 16/0051* (2013.01); *A61B 5/0536* (2013.01); *A61M 2205/502* (2013.01); *A61M 2230/65* (2013.01)

(58) Field of Classification Search
CPC .............. A63B 21/00; A61M 16/0051; A61M 2205/502; A61M 2230/65; A61B 5/0536
USPC ............ 128/204.23, 204; 600/547, 529, 533, 600/534, 536, 538
See application file for complete search history.

(56) References Cited

U.S. PATENT DOCUMENTS

| | | | | |
|---|---|---|---|---|
| 4,773,411 A | * | 9/1988 | Downs | A61M 16/00 128/204.18 |
| 5,107,830 A | * | 4/1992 | Younes | A61M 16/00 128/204.18 |
| 6,158,432 A | * | 12/2000 | Biondi | A61M 16/00 128/204.21 |
| 7,162,296 B2 | * | 1/2007 | Leonhardt et al. | 600/547 |
| 2001/0004893 A1 | * | 6/2001 | Biondi | A61M 16/00 128/204.18 |
| 2003/0159695 A1 | * | 8/2003 | Younes | A61M 16/00 128/204.18 |
| 2003/0172925 A1 | * | 9/2003 | Zocca | A61M 16/0051 128/202.22 |

(Continued)

FOREIGN PATENT DOCUMENTS

| | | |
|---|---|---|
| DE | 103 01 202 B3 | 1/2004 |
| EP | 1 000 580 A1 | 5/2000 |

OTHER PUBLICATIONS

Putensen, Christian, Wrigge Hermann, Zinserling Jörg, Electrical impedance tomography guided ventilation therapy. Current option in critical care, Jun. 2007, 13 Jg. Nr. 13, S. 344-350.

*Primary Examiner* — Andrew S Lo
(74) *Attorney, Agent, or Firm* — McGlew and Tuttle, P.C.

(57) ABSTRACT

A process is provided for operating a respirator and/or anesthesia device in the APRV mode with at least one pressure release phase with the step of setting a first point in time for terminating the pressure release phase. The process includes measuring the electrical impedance and/or impedance change of the lungs and setting the first point in time such that the measured impedance and/or impedance change are taken into account. A device is provided for carrying out the process according to the present invention.

20 Claims, 4 Drawing Sheets

(56) References Cited

U.S. PATENT DOCUMENTS

| | | |
|---|---|---|
| 2004/0133123 A1* | 7/2004 | Leonhardt .............. A61B 5/026 600/547 |
| 2006/0011195 A1* | 1/2006 | Zarychta ............... A61M 16/00 128/200.14 |
| 2006/0069326 A1 | 3/2006 | Heath |
| 2006/0155336 A1 | 6/2006 | Heath |
| 2006/0174884 A1 | 8/2006 | Habashi |
| 2007/0089744 A1* | 4/2007 | Wiese .................. A61B 5/0215 128/204.23 |

* cited by examiner

PROCESS FOR OPERATING A RESPIRATOR OR ANESTHESIA DEVICE IN THE APRV MODE TAKING INTO THE IMPEDANCE AND/OR THE IMPEDANCE CHANGE

CROSS REFERENCE TO RELATED APPLICATIONS

This application claims the benefit of priority under 35 U.S.C. § 119 of German Patent Application DE 10 2007 052 472.4 filed Nov. 2, 2007, the entire contents of which are incorporated herein by reference.

FIELD OF THE INVENTION

The present invention pertains to a process for operating a respirator (also known as a ventilator) and/or anesthesia device. The present invention pertains, furthermore, to a corresponding device.

BACKGROUND OF THE INVENTION

Figure 1A:
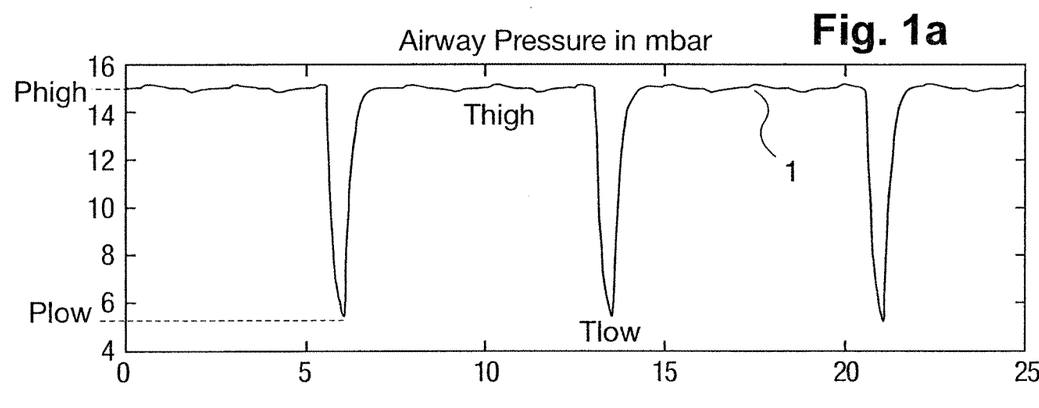
FIG. 1a is a view showing a simulation of a respiration in the APRV mode with the airway pressure in mbar as a function of the time.
Figure 1B:
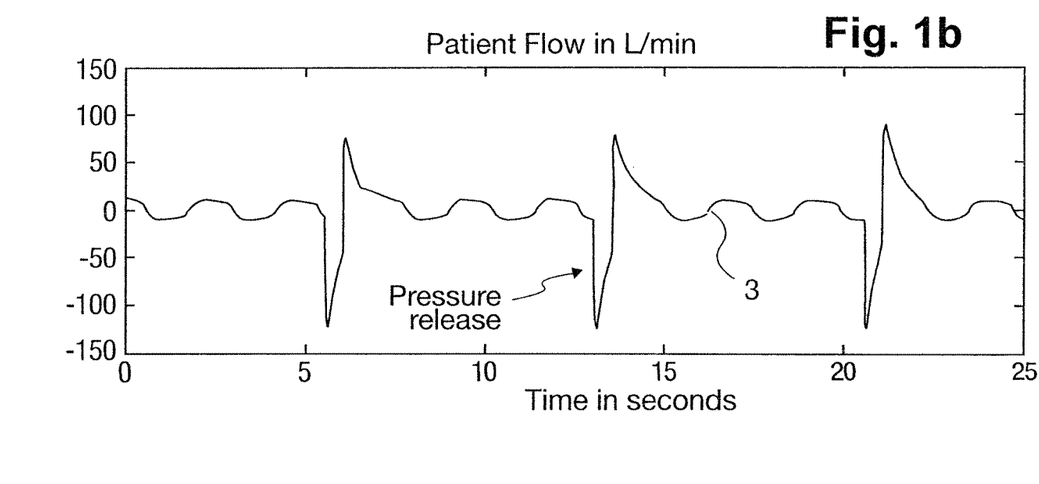
FIG. 1b is a view showing the simulation of a respiration in the APRV mode with patient flow in L/minute as a function of the time.

A respiration mode APRV (Airway Pressure Release Ventilation), which, similarly to the CPAP (Continuous Positive Airway Pressure) mode, is a mode with a continuous positive airway pressure, is known from practice. Contrary to the CPAP respiration mode, an upper pressure $P_{high}$ is applied in the APRV mode. This pressure $P_{high}$ is regularly lowered to a lower pressure level $P_{low}$ for a short duration each, and this pressure reduction is called "pressure release." The patient being respirated by means of APRV can breathe spontaneously at any time, but the pressure release is not synchronized with the patient's breathing activity. It is typical of the APRV mode that a duration $T_{high}$, during which the pressure $P_{high}$ is applied, is usually longer than a duration $T_{low}$, during which the lower pressure $P_{low}$ is present. FIGS. 1a and 1b show an example of a respiration in the APRV mode in a simulation.

During respiration in the APRV mode, the mean respiration pressure is maintained at a comparatively high level, which leads to improved oxygenation. The removal of $CO_2$ is supported by the pressure release. Due to the short duration $T_{low}$ and the short duration of pressure release, ventilation of the lungs to such an extent that alveoli would collapse and could no longer participate in the ventilation shall be prevented. The duration $T_{low}$ is set such that complete expiration is prevented from occurring. As can be recognized from FIG. 1, the pressure release is terminated before the patient flow has risen to 0 L/minute (see the times t=5.5 sec; t=13 sec; t=21.5 sec in FIG. 1).

A new set-point, which is circumscribed by "optimal flow termination based on a percentage of peak expiratory flow," is proposed for APRV respiration in the patent application US 2006/0174884 A1 of Nader M. Habashi. This set-point will hereinafter be called % PEF (Peak Expiratory Flow). The parameter % PEF is set as a percentage of a peak expiratory flow PEF. The pressure release is terminated when the instantaneous expiratory flow of the patient relative to the peak expiratory flow has dropped below the percentage set as % PEF (cf. FIG. 2). As a result, the algorithm automatically adapts the duration of the pressure release to changes in the lungs. According to the above-mentioned US 2006/0174884 A1, the end of duration $T_{low}$ shall be selected at the moment at which % PEF, which may be in a setting range between 25% and 50% of PEF (Peak Expiratory Flow), has reached or equals the set % PEF. The expiratory gas flow is monitored for this purpose, the PEF is determined, and the pressure release phase is terminated when the expiratory gas flow drops below the preset percentage % PEF.

One drawback of both a manual setting of $T_{low}$ and of an automatic adaptation of $T_{low}$ to a preset percentage of the peak expiratory flow is, however, as was described above, that this value does not represent the actual end-expiratory lung volume or the volume actually expired, but only a point in time at which it is assumed based on the reduced expiratory flow that the patient has expired to a certain extent. It is therefore not possible to evaluate whether, for example, dorsal areas of the lungs, which are under the effect of hydrostatic pressure, are effectively prevented by the termination of expiration from collapsing. In addition, in case of an existing inhomogeneity of the lung disease over the organ, there still may be lung areas that collapse during the expiration or during the pressure release phase even during expiration that is terminated already at a high percentage of the peak expiratory flow, as this is described in Habashi's US patent application. This is disadvantageous for the patient.

SUMMARY OF THE INVENTION

The object of the present invention is therefore to provide an improved process for operating a respirator and/or anesthesia device. Furthermore, the object of the present invention is to propose a corresponding respirator and/or anesthesia device.

The object according to the present invention is accomplished by a process for operating a respirator and/or anesthesia device in the APRV mode. The process according to the present invention comprises the setting of a first point in time for terminating the pressure release phase or the pressure release, wherein the first point in time takes place (is selected) such that an impedance of the patient's lungs and/or the change in this impedance is taken into account. The impedance and/or the change in the electrical impedance of the lungs are measured for this purpose. The measurement of the electrical impedance as well as of the change in that impedance is described in detail in EP 1 000 580 A1 as well as in DE 103 01 202 B3 2004.01.22. The related disclosure contents of these documents become the subject of the present invention by reference (EP 1 000 580 A1 as well as DE 103 01 202 B3 2004.01.22 are incorporated herein by reference in their entirety).

An advantage associated with the process according to the present invention is that ventilation processes within the lungs as well as in individual sections of the lungs are detected in space. These ventilation processes are reflected in the form of the impedance change, from which the change in volume within the lungs can be inferred. Not only the extent, but rather also the distribution in space of the change in volume within the lungs during ventilation and especially during the pressure release phase can be evaluated in this manner. $T_{low}$ can be optimized on the basis of this information.

The impedance measurement can be calibrated here by relating a global impedance change to the volume breathed during spontaneous respiration at the pressure level $P_{high}$. The volume, which is corrected by the compliance of the flexible tube system and possible leaks and which is actually available for filling the patient's lungs, can now be taken into account. The user is thus able to preset an actual expiration volume, which must not be exceeded. The expiration can be advantageously terminated when the corresponding global impedance change is reached.

It is also possible to limit the expiration or to terminate the pressure release by means of the present invention when a determined impedance drops—globally or locally or regionally—below a certain value or is leaving or has left a preset range.

The term "first point time" is defined according to the present invention as the point in time at which measures, which are associated with the termination of the pressure release phase and which signify the transition to inspiration, are taken on the device for the first time within a respiration cycle. Termination of the pressure release phase may take place, for example, due to the closing of an expiration valve of the respirator and/or anesthesia device being used at a set, first point in time. The termination of the pressure release phase may also be "announced" by the application of an inspiration flow or the like. However, the "first point in time" may also be defined as the point in time at which it was determined that the pressure release should now be terminated. Furthermore, "first point in time" may also be defined as such a point in time at which not necessarily the first, but an essential measure is taken to terminate the pressure release or the pressure release phase.

A patient is defined according to the present invention both as a human patient and as an animal to be treated.

"Measurement of the change in impedance and/or of the impedance change" is defined according to the present invention as a single-time or repeated measuring operation.

Provisions are made in another preferred embodiment of the process according to the present invention for the first point in time, at which the pressure release phase shall be terminated, to be placed to the point in time at which a regional impedance change in the lungs exceeds a global impedance change of the lungs by a predetermined extent.

A regional impedance change of the lungs is defined as a change in impedance in a certain (partial) area of the lungs. This area may be predetermined by the user. The (partial) area may correspond to certain anatomic structures, such as the lower lobe of the right lung and/or the lower lobe of the left lung. However, it may also correspond to a functional unit or simply to any desired specification, e.g., a dorsal marginal area of the lung, which is closest to a bed for the patient being respirated. The (partial) area may also be a layer changing from one breath to the next or a changing volume in the lung, which may be characterized, e.g., by especially great changes in impedance compared to other areas of the lungs.

A "global impedance change" is defined as an impedance change in the entire lung, optionally also the impedance change in all other areas of the lung only, i.e., without inclusion of the—regional—(partial) lung areas.

Thus, it is possible according to the present invention to recognize, e.g., an imminent collapse of alveoli in a regional area in time on the basis of the impedance change increasing excessively there or based on the fact that absolute impedance values have been reached, and to take appropriate measures, e.g., to terminate the pressure release phase. Maximum gas exchange is permitted in this manner, while alveoli in certain regional areas are prevented from collapsing.

If the impedance changes uniformly essentially over the entire lung, it is assumed that the change in volume takes place because of tidal ventilation. The risk of collapse is thus recognized as being lower here. The pressure release does not have to be terminated prematurely.

The statements made above also apply to the case in which a regional impedance exceeds a predetermined extent of a global impedance.

According to the criterion of another preferred embodiment, according to which a regional impedance change is related to a global impedance change and thus must not exceed a predetermined extent, the first point in time is set as having been reached and the pressure release is terminated in case of an impedance change in, e.g., a lower area of the lung cross section that exceeds 100%, 120%, 125% or 130% or more, but especially 125% of the impedance change of the entire lung cross section. This value was recognized by the inventors as being especially advantageous and safe for the patient for protection against collapse of dorsal alveoli.

In yet another preferred embodiment, the first point in time is set at the point in time at which the global impedance change and/or the global impedance exceed an amount predetermined by the user.

This may be by stating a value for the permissible impedance change and/or impedance itself. This value may concern, e.g., the global impedance change, i.e., the impedance change for the entire lung, or a regional impedance change, i.e., an impedance change of only one area, as was described above.

In addition, as in every other embodiment regardless of other features, the termination of the pressure release phase or the offset of the first point in time can take place in this embodiment when, contrary to an impedance change, an absolute value for the impedance is exceeded.

If, by contrast, the user specifies a volume to be expired for the pressure release phase, this volume can be converted, by relating it to the impedance or volume change occurring during a preceding ventilation, into an impedance change or into an absolute value for an impedance, and the respirator or anesthesia device can be operated correspondingly.

In yet another preferred embodiment according to the present invention, the impedance and/or the impedance change of the lungs is determined from at least one impedance tomogram.

As is proposed in yet another preferred embodiment, the impedance change and/or impedance measured in an image section of the impedance tomogram can be used as a local impedance change or impedance. The impedance change or impedance measured in the impedance tomogram of the entire lung can now be used as a global impedance change or impedance in the further process.

As is proposed in yet another preferred embodiment, the impedance change measured in a lower quarter of the impedance tomogram or of the lung cross section can be used as a local impedance change. This also applies to the impedance, contrary to the impedance change. Such a division of the lung cross section into quarters is, however, arbitrary. A division into thirds or fifths and the like is also covered by the present invention. In case of division into quarters—or into any desired number of parts—this may also concern according to the present invention the entire area of the impedance tomogram. However, it may also be related to the lung area actually present in the cross section, as is shown in the tomogram.

If it is assumed in an example that the termination criterion for the pressure release phase is set at, e.g., 125%, as was described above, the pressure release is terminated in the APRV mode when the ratio of the measured impedance changes (regional to global) assumes this value. The expiration valve must be closed and an inspiration flow must be applied at this moment in order to achieve a pressure rise in the respiration system. However, it is known from practice that a valve always closes and opens with a time delay. In addition, system delays can be observed during the processing and passing on of information, e.g., the signal to the expiration valve. These delays cause, in their sum, that the lung can continue to empty during the time that is due to these delays. The actual closing value of the expiration valve could consequently be markedly higher than this value in the example of the 125% value set. However, since an arbitrary emptying must not take place for the above-mentioned reasons, another preferred embodiment of the process according to the present invention proposes a control, with which it can be advantageously ensured that the pressure release phase will indeed also be terminated at the intended point in time. Advantageous variants of this process are also described.

A patent application has already been filed by the applicants of the present application for this process with the German Patent and Trademark Office. The application bears the application number 10 2007 026 036.0. Reference is herewith made expressly to the related disclosure of this application. The related contents of that application are thus part of the present disclosure by reference.

The object according to the present invention is accomplished, furthermore, by an anesthesia device and/or respirator with means for carrying out the process. Since all the above-mentioned advantages can be gained to the full extent by means of the device, reference is expressly made here to the above discussion in order to avoid repetitions.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings in particular, FIGS. 1a and 1b show an example of a respiration in the APRV mode in a simulation, wherein the view at the top (FIG. 1a) shows the airway pressure 1 in mbar, and the view at the bottom (FIG. 1b) shows the corresponding patient flow 3 in L/minute, both as a function of the time. The airway pressure 1 varies here between an upper pressure level $P_{high}$ and a lower pressure level ($P_{low}$. The pressure level $P_{high}$ is applied here over a duration $T_{high}$, and the lower pressure level $P_{low}$ over a duration $T_{low}$. One of three pressure release phases is marked by an arrow in the view at the bottom of FIG. 1.

Figure 2:
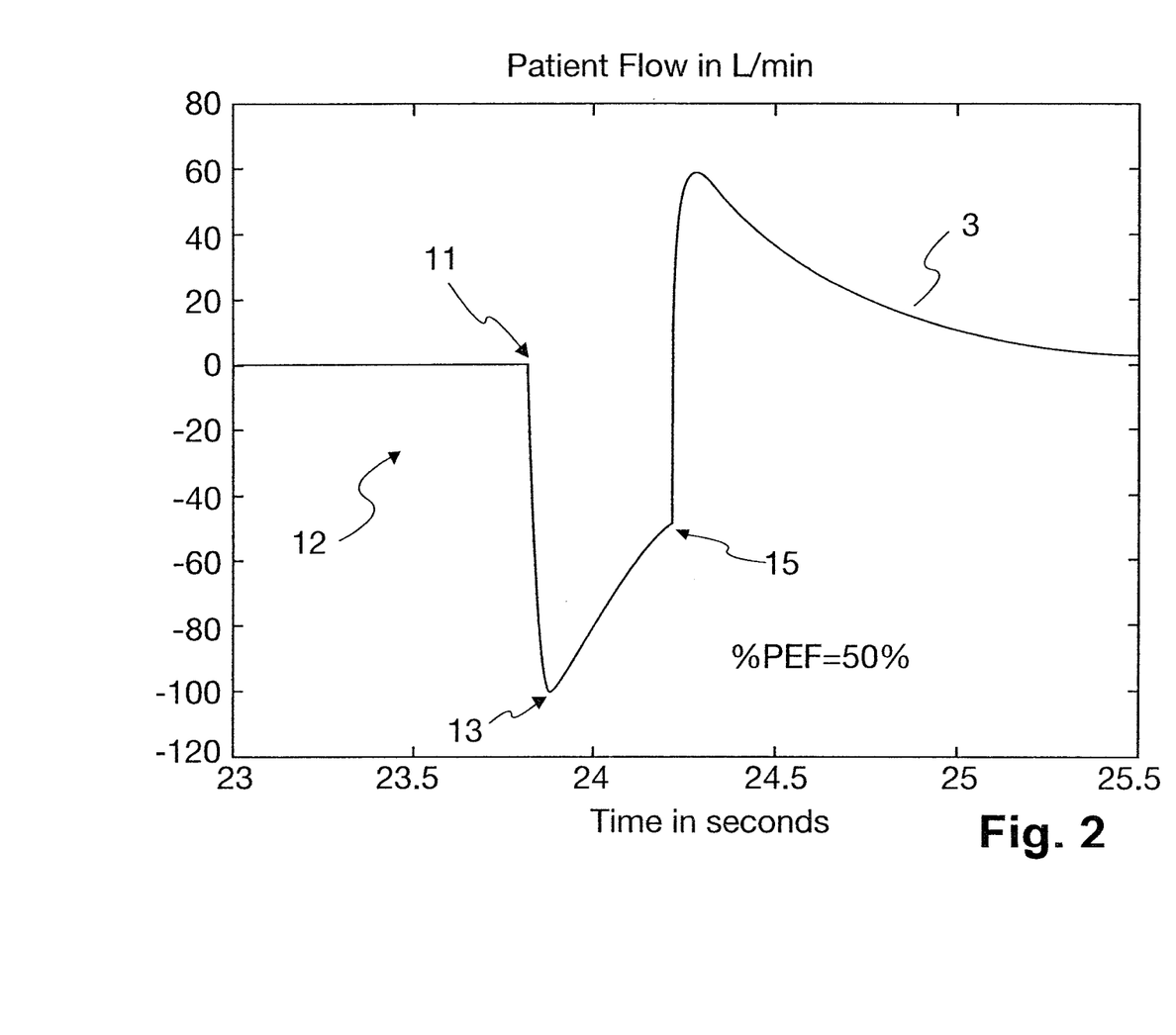
FIG. 2 is a view showing respiration scheme in the APRV mode with a % PEF criterion.

FIG. 2 shows the patient flow 3 as a function of time in a simulation of an APRV respiration. A point in time 11, at which a pressure release phase 12 is begun, is indicated in FIG. 2. FIG. 2 shows, furthermore, a point in time 13, at which a peak flow—in this case at the level of 100 L/minute—is reached. Moreover, FIG. 2 shows a point in time 15, at which the pressure release phase 12 is terminated at a set % PEF of 50%.

Figure 3A:
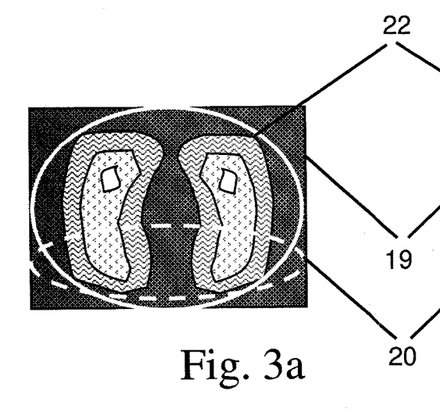
FIG. 3a is a view of an impedance tomogram for use in the process according to the present invention.
Figure 3B:
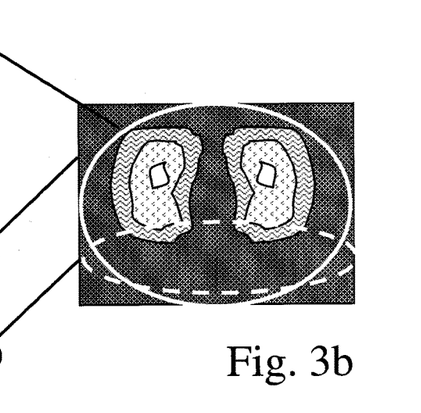
FIG. 3b is a view of an impedance tomogram for use in the process according to the present invention.
Figure 3C:
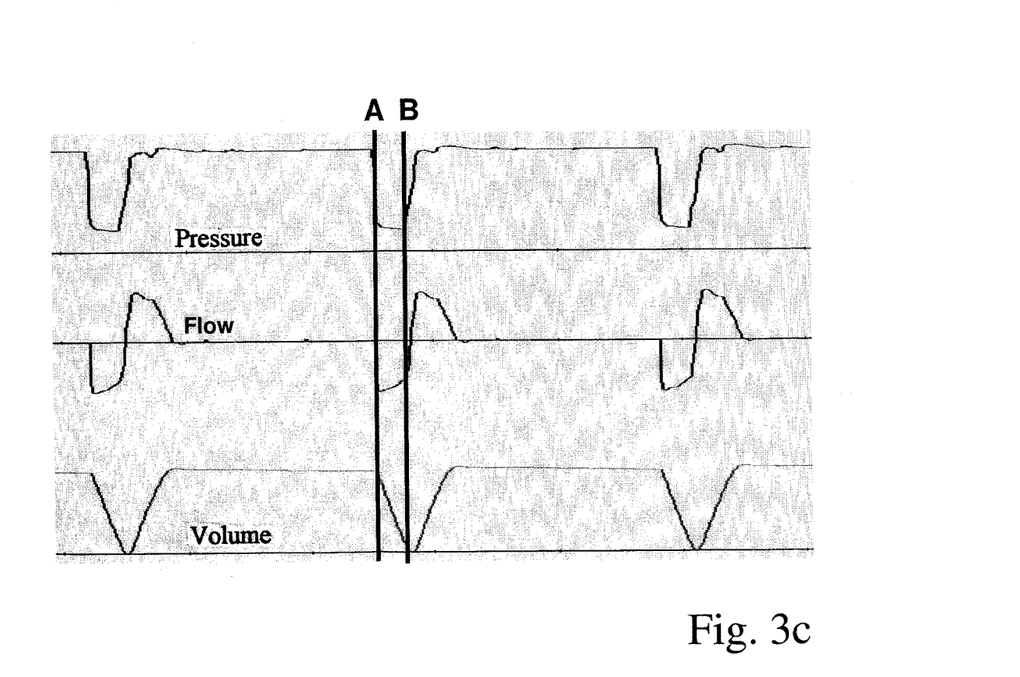
FIG. 3c is a view showing pressure, flow and volume conditions corresponding to the impedance tomogram views of FIG. 3a and 3b.

FIG. 3a shows the cross section of a more or less homogeneously ventilated lung in an impedance tomographic view 19. Ventilation taking place tidally is assumed for the view in FIG. 3a. Ventilation is promoted, on the one hand, with the short-term "releases," which are shown between the markings A and B in FIG. 3c, which shows the pressure, flow and volume conditions in the lungs or in the respiration system, and derecruitment is also avoided, on the other hand, by limiting $T_{low}$ to the period between A and B. Such a derecruitment usually begins in the dorsal regions of the lung of a lying patient, as it can be recognized in the lower area of the view in FIG. 3b from the changed brightness of the view compared to FIG. 3a or the color-coded view of the impedance change in the lower, dorsal areas 20.

If the relative change in impedance in a lower area 20 (surrounded by broken lines in FIGS. 3a and 3b) is related to the change in the total impedance (or global impedance), measured in the area 22 not enclosed by broken lines, the $T_{low}$ at which dorsal atelectases begin to form can be recognized in time. $T_{low}$ can be correspondingly regulated such that the gas exchange is maximized but derecruitment is minimized.

Figure 4:
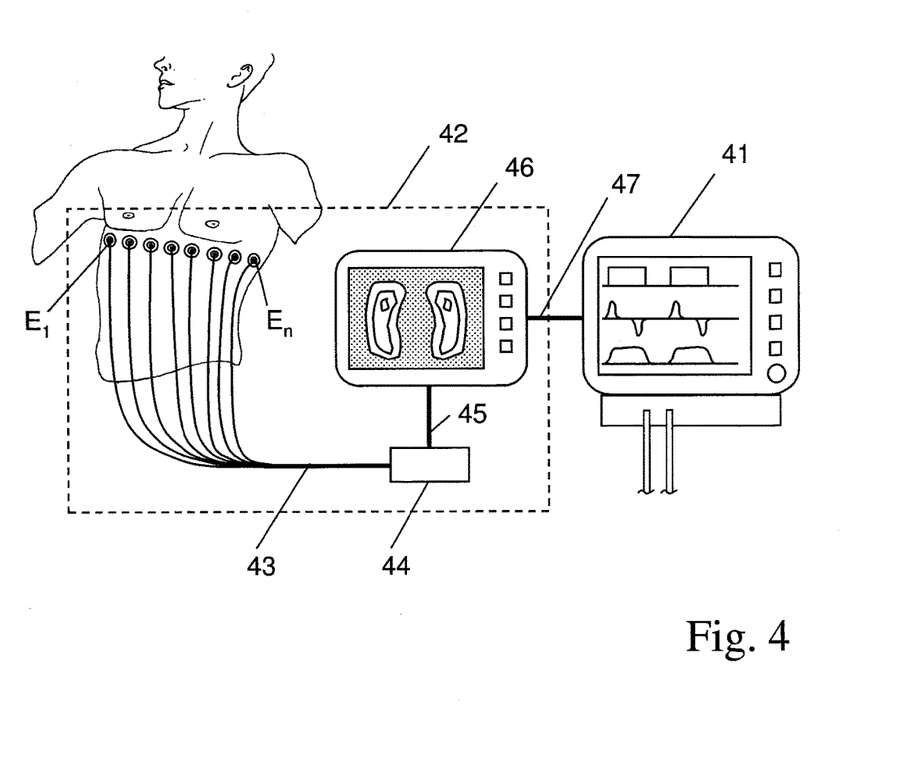
FIG. 4 is a schematic view showing an exemplary embodiment of a device according to the present invention for carrying out the process according to the present invention.

FIG. 4 shows an example of an external first measuring system 42 for electrical impedance tomography (abbreviated as EIT), which is connected to a respiration system 41 by means of an electrical line connection 47. This electrical connection 47 is used for the bidirectional data exchange and optionally for the energy supply for the EIT measuring system 42. The EIT measuring system 42 has a plurality of electrodes E1 through $E_n$, especially 16 or 32, which are preferably arranged in an electrode belt and can be fastened especially equidistantly on the patient's thorax. One electrode pair each, which is connected so as to consecutively encircle the body, is used to feed a weak alternating current of a few mA, while the respective other electrodes are used to measure the surface potentials in order to ultimately calculate the impedance distribution in the body relative to a section plane of the electrodes.

The electrodes E1 through $E_n$ are connected by means of analog connection line 43 to an analog-digital adaptation circuit (interface) 44, which contains, in general, power sources, measuring amplifiers, analog-digital and digital-analog converters as well as computing units. Interface 44 is connected by means of a first digital connection line 45 to a monitor 46 of the EIT measuring system 42, so that the impedance values can be displayed on the display screen. The views show space- and time-resolved distributions of the lung ventilation as well as blood and serum changes, so that physiological changes in the patient can be detected and possibly monitored.

The respiration system 41 shown schematically is used to respirate a patient and has, in general, a breathing gas metering and/or a breathing gas delivery means as well as measuring and control means in order to respirate the patient according to a preset, stored respiration curve, for example, in a pressure- or volume-controlled manner. Data can be exchanged between the EIT measuring system 42 and the respiration system 41 bidirectionally by means of the electrical line connection 47. For example, impedance data can thus be transmitted from the EIT measuring system 42 to the respiration system 41.

The electrical line connection 47 preferably has a standardized interface component each, for example, Ethernet, in both the EIT measuring system 42 and the respiration system 41.

Other embodiments of the device according to the present invention, with which the process according to the present invention can be carried out, are described in DE 103 01 202 B3 2004.01.22, which was already cited above. The relative contents thus become a disclosure of the present application.

A determination of the optimal point in time as the first point in time for terminating the expiration, i.e., the end of time $T_{low}$ during respiration in the APRV mode according to the present invention can be carried out on the basis of a global impedance change, which takes place based on an expiratory tidal volume entered by the user and a "calibration" of the impedance change per unit of change in the tidal volume based on the flow and volume.

However, the first point in time can also be set by the user setting a global impedance change recognized before as optimal on the respirator (e.g., by inputting) after he or she had manually optimized the time $T_{low}$ before. The end-expiratory lung volume determined during the manual optimization can thus be maintained uniformly by means of monitoring of the global impedance or the change in the global impedance by making provisions for a corresponding limitation of the impedance change. This also applies to the impedance as a reference value (contrary to the impedance change).

A $V_{pat}/Z_{global}$ value is obtained by integrating the patient gas flow during an inspiration and relating this to the global impedance change of the same breath. Taking this relationship into account, $T_{low}$ can be controlled such that an expiratory tidal volume $V_{ex}$ explicitly preset by the user is obtained. The advantage of the use of the impedance change as distinguished from the volume change is—assuming a valid determination of $V_{pat}/Z_{global}$—the independence from interference variables such as leakage or tube compliance, because the impedance change is proportional to the volume actually being moved, relative to the patient's lungs.

Thus, the present invention proposes, for the first time ever, a process for operating a respirator and/or anesthesia device in the APRV mode with at least one pressure release phase with the step of setting a first point in time for terminating the pressure release phase, measurement of the electrical impedance and/or impedance change of the lungs and setting of the first point in time taking into account the measured impedance and/or impedance change. The present invention proposes, furthermore, a device for carrying out the process according to the present invention.

While specific embodiments of the invention have been shown and described in detail to illustrate the application of the principles of the invention, it will be understood that the invention may be embodied otherwise without departing from such principles.

What is claimed is:

1. A process for in Airway Pressure Release Ventilation (APRV) mode with at least one pressure release phase, the process comprising the steps of:

providing a measuring system for measuring the impedance and/or the impedance change of the patient's lungs;

measuring with the measuring system the impedance and/or the impedance change of the lungs of the patient being respirated; and setting a first point in time for terminating the pressure release phase based on the measured impedance and/or impedance change.

2. A process in accordance with claim 1, wherein said step of setting the first point in time occurs at least one of:

when a regional impedance change in the lung exceeds a global impedance change of the lung by a predetermined extent, and when a regional impedance of the lung exceeds a global impedance of the lung by a predetermined extent.

3. A process in accordance with claim 2, wherein the step of setting the first point in time occurs when the impedance change in a lower area of a lung cross section exceeds a predetermined percentage of the impedance change of an entire lung cross section.

4. A process in accordance with claim 3, wherein said predetermined percentage is one of 100%, 110%, 120% and 125%.

5. A process in accordance with claim 3, wherein said first point in time is set to when the global impedance change exceeds a value preset by a user and/or the global impedance rises above a preset amount.

6. A process in accordance with claim 1, wherein a predetermined value for a volume to be expired for the pressure release phase is converted into an impedance and/or an impedance change used for setting the first point in time.

7. A process in accordance with claim 1, wherein said step of measuring includes determining the impedance and/or the impedance change of the lung from at least one impedance tomogram.

8. A process in accordance with claim 7, wherein the impedance and/or impedance change measured in an image section of the impedance tomogram is used as a local impedance and/or impedance change and the impedance and/or impedance change measured in the impedance tomogram of an entire lung is used as a global impedance and/or impedance change.

9. A process in accordance with claim 7, wherein the impedance and/or impedance change measured in a lower quarter of the impedance tomogram or of a lung cross section is used as a local impedance and/or impedance change.

10. A process in accordance with claim 1, further comprising the step of:

initiating a respiration process at the first point in time, wherein at least one effect of the respiration process begins at a second point in time following the first point in time;

determining the impedance present at the second point in time and/or the impedance change and/or a ratio of the regional impedance change to the global impedance change; and controlling the actual impedance and/or the impedance change and/or the ratio of the regional impedance change to the global impedance change to the set impedance and/or the impedance change and/or the ratio of the regional impedance change to the global impedance change or controlling the set impedance and/or the impedance change and/or the ratio of the regional impedance change to the global impedance change to the actual impedance and/or the impedance change and/or the ratio of the regional impedance change to the global impedance change.

11. A process in accordance with claim 10, further comprising the step of:
controlling the actual impedance and/or the impedance change and/or the ratio of the regional impedance change to the global impedance change to the set impedance and/or the impedance change and/or the ratio of the regional impedance change to the global impedance change by bringing forward in time the initiation of the respiration process to a third point in time such that the effect of the respiration process begins at the first point time.

12. A process in accordance with claim 10, further comprising the step of:
calculating a deviation between the actual impedance and/or impedance change and/or the ratio of the regional impedance change to the global impedance change and the set impedance and/or the impedance change and/or the ratio of the regional impedance change to the global impedance change.

13. A process in accordance with claim 12, further comprising the step of:
filtering and/or limiting the deviation.

14. A process in accordance with claim 12, further comprising the step of:
calculating a control offset as a sum of a control offset of an earlier point in time and the deviation.

15. A process in accordance with claim 14, further comprising the step of:
filtering and/or limiting the control offset.

16. A process in accordance with claim 15, further comprising the step of:
calculating a percentage to be applied as a sum of the set impedance and/or the impedance change and/or the ratio of the regional impedance change to the global impedance change and the control offset.

17. A process for ventilating a patient in Airway Pressure Release Ventilation (APRV) mode, the process comprising the steps of:
supplying breathing gas to lungs of the patient at a high pressure for a high pressure time;
supplying breathing gas to the lungs of the patient at a low pressure;
measuring an impedance of the lungs of the patient during said supplying at the low pressure, said measuring of the impedance includes measuring a global impedance of the lungs and a regional impedance of the lungs;
switching said supplying of breathing gases between the low pressure and the high pressure, said switching including selectively switching from said supplying at the low pressure to said supplying at the high pressure based on a relationship of the regional impedance and the global impedance.

18. A process in accordance with claim 17, wherein:
said measuring of the impedance includes measuring a plurality of impedances at several points in time during said supplying of the breathing gases at the low pressure;
said switching of said supplying from the low pressure to the high pressure occurring when one of the measured impedances fulfills a predetermined criteria.

19. A process in accordance with claim 17, wherein:
said switching of said supplying from said supplying at the low pressure to said supplying at the high pressure occurs when the regional impedance exceeds the global impedance.

20. A process in accordance with claim 17, wherein:
said switching of said supplying from said supplying at the low pressure to said supplying at the high pressure occurs when the change in the regional impedance exceeds the change in the global impedance.

* * * * *